United States Patent
Murakami et al.

(10) Patent No.: US 8,623,782 B2
(45) Date of Patent: Jan. 7, 2014

(54) PROCESS FOR PREPARING COPPER-BASED CATALYST, COPPER-BASED CATALYST, AND PRETREATMENT METHOD OF THE SAME

(75) Inventors: Masami Murakami, Ichihara (JP); Ken Maeda, Ichihara (JP); Yuya Goto, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 140 days.

(21) Appl. No.: 13/202,266

(22) PCT Filed: Feb. 15, 2010

(86) PCT No.: PCT/JP2010/052211
§ 371 (c)(1),
(2), (4) Date: Aug. 18, 2011

(87) PCT Pub. No.: WO2010/095599
PCT Pub. Date: Aug. 26, 2010

(65) Prior Publication Data
US 2011/0301022 A1 Dec. 8, 2011

(30) Foreign Application Priority Data

Feb. 23, 2009 (JP) .................................. 2009-040055
Feb. 23, 2009 (JP) .................................. 2009-040056
Feb. 23, 2009 (JP) .................................. 2009-040057

(51) Int. Cl.
*B01J 23/70* (2006.01)
*B01J 23/72* (2006.01)
*B01J 21/00* (2006.01)
*B01J 23/02* (2006.01)
*B01J 23/06* (2006.01)
*B01J 23/04* (2006.01)
*B01J 23/00* (2006.01)

(52) U.S. Cl.
USPC ........... 502/345; 502/244; 502/340; 502/341; 502/344; 502/349; 502/355

(58) Field of Classification Search
USPC .......... 502/244, 340, 341, 344, 345, 349, 355
See application file for complete search history.

(56) References Cited

U.S. PATENT DOCUMENTS 3,303,001 A    2/1976   Dienes
4,102,814 A *   7/1978   Gustin .......................... 436/155
(Continued)

FOREIGN PATENT DOCUMENTS

CN         1219445      6/1999
JP         52-076288     6/1977
(Continued)

OTHER PUBLICATIONS

International Search Report dated May 18, 2010.
(Continued)

*Primary Examiner* — Anthony J Zimmer
(74) *Attorney, Agent, or Firm* — Rankin, Hill & Clark LLP

(57) ABSTRACT

There is provided by the present invention a process for preparing a copper-based catalyst having good catalytic activity, markedly excellent durability and good reproducibility. The process for preparing a copper-based catalyst of the invention is a process for preparing a catalyst composed of metal oxides containing copper oxide as an essential component and is characterized by comprising the following steps: (1) a step of bringing an acidic metal salt solution containing copper and a precipitant solution into contact with each other to obtain a slurry solution containing a precipitate of a catalyst precursor, and (2) a step of continuously bringing the slurry solution and a wash liquid into contact with each other to wash the precipitate, with substantially keeping the suspended state.

13 Claims, 1 Drawing Sheet

(56) References Cited

U.S. PATENT DOCUMENTS

| | | |
|---|---|---|
| 4,596,782 A | 6/1986 | Courty et al. |
| 6,048,820 A | 4/2000 | Takeuchi et al. |
| 6,114,279 A | 9/2000 | Fukui et al. |

FOREIGN PATENT DOCUMENTS

| | | |
|---|---|---|
| JP | 60-190232 | 9/1985 |
| JP | 63-039287 | 2/1988 |
| JP | 06-254414 | 9/1994 |
| JP | 06-312138 | 11/1994 |
| JP | 07-008799 | 1/1995 |
| JP | 07-039755 | 2/1995 |
| JP | 10-272361 | 10/1998 |
| JP | 10-309466 | 11/1998 |
| JP | 2004-298685 | 10/2004 |
| JP | 2007-083197 | 4/2007 |

OTHER PUBLICATIONS

Chinese Office Action issued in connection with the corresponding application (No. 201080007274.3) dated Jan. 14, 2013.

Shokubai Koza (Lectures of Catalysts), vol. 7, edited by Catalysis Society of Japan, issued by Kodansha Ltd. on Jul. 20, 1989, pp. 21-39 with partial English translation.

Applied Catalysis A: General, 138 (1996), pp. 311-318.

* cited by examiner

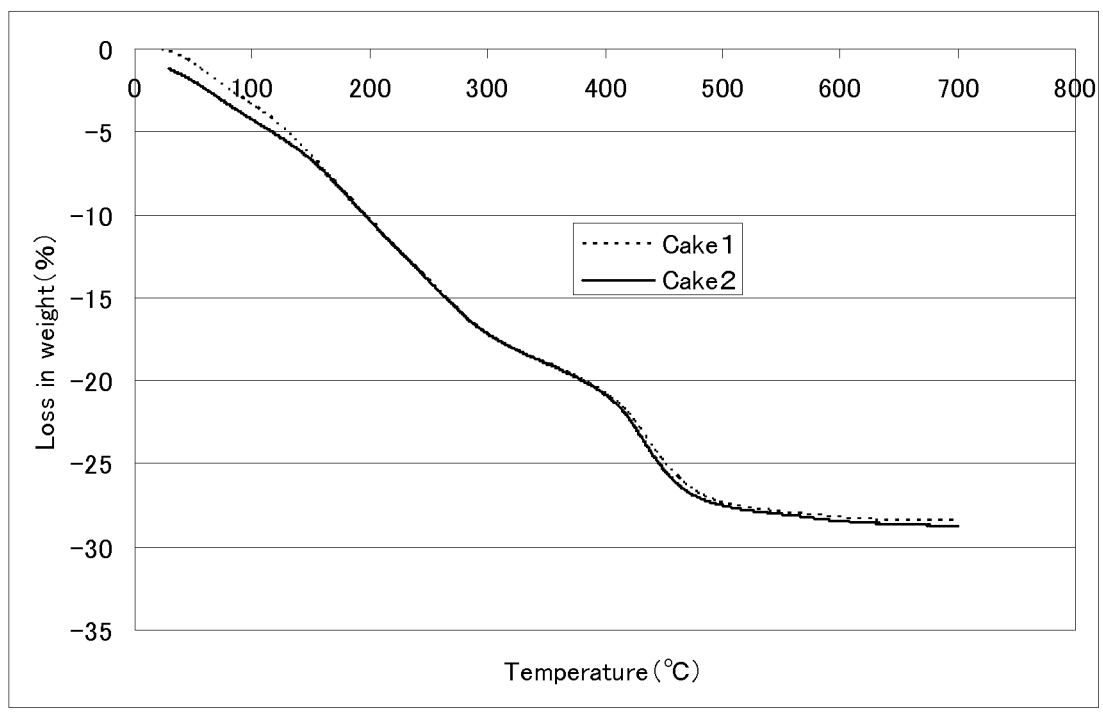

PROCESS FOR PREPARING COPPER-BASED CATALYST, COPPER-BASED CATALYST, AND PRETREATMENT METHOD OF THE SAME

TECHNICAL FIELD

The present invention relates to a process for preparing a copper-based catalyst which is used for methanol synthesis reaction or its reverse reaction, methanol reforming reaction, shift reaction or its reverse reaction, etc., a copper-based catalyst and a pretreatment method of the copper-based catalyst. More particularly, the invention relates to a process for preparing a copper-based catalyst which is useful for synthesizing methanol from hydrogen and carbon oxide ($CO_2$ alone or mixed gas of $CO_2$ and CO), a copper-based catalyst and a pretreatment method of the copper-based catalyst.

BACKGROUND ART

Methanol synthesis process using a synthetic gas (mixed gas of CO and $H_2$) as a main raw material (containing a small amount of $CO_2$) is a basic process that is extremely important in chemical industry, and increase of efficiency of the process has been always desired in the past from the viewpoints of energy saving, economy, etc. One of the most important techniques in the methanol synthesis process is to provide a catalyst of high performance. As conventional catalysts, three-component catalysts, such as $Cu/ZnO/Al_2O_3$ catalyst (catalyst for industry at present, e.g., "Shokubai Koza (Lectures of Catalysts)", vol. 7, edited by Catalysis Society of Japan, issued by Kodansha Ltd. on Jul. 20, 1989, pp. 21-39 (non-patent document 1)) and $Cu/ZnO/SiO_2$ catalyst (JPA-1988-39287 (patent document 1)), are known.

On the other hand, methanol synthesis using $CO_2$ and $H_2$ as main raw materials has been particularly paid attention recently from the viewpoints of recycling of carbon resources and global environmental problem. In the synthesis of methanol from a raw material gas having a high content of $CO_2$, a catalyst having higher activity than a catalyst adopted in the synthesis of methanol from the above synthetic gas has been desired because of thermodynamic equilibrium of the reaction and the reaction inhibition effect of water formed together with methanol (Applied Catalysis A: General, 38 (1996), pp. 311-318 (non-patent document 2)). In the synthesis of methanol from a raw material gas having a high content of $CO_2$, lowering of catalytic activity presumed to be attributable to water formed together with methanol is very severe as compared with that in the synthesis of methanol from a synthetic gas. On that account, a catalyst having much higher durability than a catalyst adopted in the synthesis of methanol from a synthetic gas has been desired. The reason is that the three-component catalysts adopted in the above methanol synthesis are insufficient in the catalytic performance.

From such viewpoints, copper-based multi-component catalysts obtained by further adding components, such as copper/zinc oxide/aluminum oxide/zirconium oxide catalyst and copper/zinc oxide/aluminum oxide/zirconium oxide/gallium oxide catalyst, have been developed (see, e.g., JPA-1995-39755 (patent document 2), JPA-1994-312138 (patent document 3), Applied Catalysis A: General, 38 (1996), pp. 311-318 (non-patent document 2)). Moreover, a catalyst of high activity obtained by adding 0.3 to 0.9% by weight of colloidal silica or water-dissolved silica as silica and calcining the resulting product at 480 to 690° C. has been developed (JPA-1998-309466 (patent document 4)).

These catalysts have high activity, but the activity is not necessarily reproduced sufficiently in some cases even if they are prepared by the same formulation. It is generally known that stable pH in the precipitation step and sufficient washing of a precipitant are necessary in order to obtain a catalyst of high activity with good reproducibility (e.g., JPA-1977-76288 (patent document 5), JPA-1995-8799 (patent document 6), JPA-2007-83197 (patent document 7)). A large number of improving methods for that have been carried out, but it cannot be necessarily said that their reproducibility is good, and further improvement has been desired.

The above catalysts are useful because of high activity. However, the preparation steps include, for example, precipitation, aging, washing, filtration, drying, molding and calcining, and become long. In the industrial production, therefore, it is preferable to simplify the preparation steps, however little, to thereby reduce a burden in the production, and such improvement has been also desired.

It is known that the main cause of such lowering of catalytic activity of the copper-based catalyst is decrease of surface area due to sintering of copper. It is known that copper is a metal readily undergoing sintering among various metal catalysts, and it is necessary that the reduction temperature of a catalyst before the reaction and the reaction temperature should not be raised. For example, it is described in JPA-2004-298685 (patent document 8) that the reduction temperature of a Cu/ZnO catalyst is in the range of preferably 100 to 300° C., more preferably 150 to 250° C.; it is described in JPA-1994-254414 (patent document 9) that the reduction temperature of a $Cu/ZnO/ZrO_2$ catalyst is in the range of preferably 100 to 300° C., more preferably 120 to 200° C.; and it is described in JPA-2007-83197 (patent document 7) that the reduction temperature of a $Cu/ZnO/Al_2O_3$ catalyst is in the range of preferably 100 to 300° C., more preferably 110 to 280° C., still more preferably 130 to 240° C. The reason is that if the reduction temperature is raised too high, the copper surface area is decreased by sintering of copper. Accordingly, improvement in the pretreatment method (reduction method) of a copper-based catalyst which does not cause sintering of copper has been also desired.

CITATION LIST

Patent Literature

Patent document 1: JPA-1988-39287
Patent document 2: JPA-1995-39755
Patent document 3: JPA-1994-312138
Patent document 4: JPA-1998-309466
Patent document 5: JPA-1977-76288
Patent document 6: JPA-1995-8799
Patent document 7: JPA-2007-83197
Patent document 8: JPA-2004-298685
Patent document 9: JPA-1994-254414

Non-Patent Literature

Non-patent document 1: Shokubai Koza (Lectures of Catalysts), vol. 7, edited by Catalysis Society of Japan, issued by Kodansha Ltd. on Jul. 20, 1989
Non-patent document 2: Applied Catalysis A: General, 38 (1996), pp. 311-318

SUMMARY OF INVENTION

Technical Problem

The present invention has been made in the light of such circumstances as mentioned above. It is an object of the present invention to provide a process for preparing a copper-based catalyst which exhibits good catalytic activity, markedly excellent durability and good reproducibility in catalytic reactions, such as methanol synthesis reaction or its reverse reaction, methanol reforming reaction, and shift reaction or its reverse reaction, and a copper-based catalyst. It is also an object of the present invention to provide a process for preparing a copper-based catalyst, comprising more simplified preparation steps than those of conventional processes, and a pretreatment method of a copper-based catalyst, which does not bring about lowering of catalytic activity.

Solution to Problem

In order to solve the above problems, the present inventors have earnestly studied. As a result, they have found that the above problems can be solved by carrying out (1) a step of continuously bringing an acidic metal salt solution containing copper and a precipitant solution into contact with each other to obtain a slurry solution containing a precipitate of a catalyst precursor, and (2) a step of bringing the slurry solution and a wash liquid into contact with each other to wash the precipitate, with substantially keeping the suspended state, and they have accomplished the present invention.

In particular, the present inventors have found that (1) by bringing a slurry given in the course of the catalyst preparation into contact with water under the specific conditions, a copper-based catalyst having good catalytic activity, markedly excellent durability and good reproducibility is obtained, (2) by controlling a water content in the drying step of the catalyst preparation, a copper-based catalyst having good catalytic activity and durability can be prepared with high productivity without carrying out steps of addition of water and standing which have been carried out in conventional preparation processes, and (3) by the pretreatment method wherein reduction reaction is carried out in the specific temperature range, a copper-based catalyst having good catalytic activity and markedly excellent durability is obtained.

As described in the above (3), the present inventors have found that in the case of the copper-based catalyst obtained by the above preparation process (particularly, copper-based catalyst composed of metal oxides containing copper oxide, zinc oxide and aluminum oxide as essential components and containing zirconium oxide, gallium oxide and silicon oxide as arbitrarily components), sintering hardly takes place even if reduction is carried out at a high temperature, or rather, pretreatment wherein reduction is carried out at a high temperature makes it possible to obtain a copper-based catalyst which exhibits excellent durability in methanol synthesis reaction using $CO_2$ and $H_2$ as main raw materials, and other reactions.

That is to say, the process for preparing a copper-based catalyst of the invention is a process for preparing a catalyst composed of metal oxides containing copper oxide as an essential component and is characterized by comprising the following steps: (1) a step of bringing an acidic metal salt solution containing copper and a precipitant solution into contact with each other to obtain a slurry solution containing a precipitate of a catalyst precursor, and (2) a step of continuously bringing the slurry solution and a wash liquid into contact with each other to wash the precipitate, with substantially keeping the suspended state.

The catalyst composed of metal oxides containing copper oxide as an essential component preferably further contains at least one oxide selected from zinc oxide, aluminum oxide, zirconium oxide, gallium oxide and silicon oxide.

The catalyst composed of metal oxides containing copper oxide as an essential component is preferably a catalyst composed of metal oxides containing copper oxide, zinc oxide and aluminum oxide as essential components and containing zirconium oxide, gallium oxide and silicon oxide as arbitrary components.

The wash liquid is preferably water.

It is preferable that the acidic metal salt solution containing copper and the precipitant solution are both aqueous solutions, and after these aqueous solutions are mixed in water to form a precipitate of a catalyst precursor in the step (1), dissolution equilibrium of an alkali metal of the precipitant component is sufficiently reached in such a state that the precipitate is highly dispersed in water, and the slurry solution and a wash liquid comprising water are brought into contact with each other to wash the precipitate, with substantially keeping the suspended state, in the step (2).

It is preferable that the step (2) includes a step of continuously carrying out drawing of the slurry liquid phase portion and feeding of the wash liquid comprising water to remove the alkali metal of the precipitant component, and the step (2) is followed by (3) a step of drawing the slurry liquid phase portion outside the system without adding water to thereby increase the concentration of the catalyst precursor contained in the slurry solution and to obtain a precipitate in the form of a cake, and (4) a step comprising drying and calcining the precipitate in the form of a cake to obtain metal oxides.

It is preferable that the precipitant is an alkali metal salt, and the alkali metal is removed until the concentration of the alkali metal contained in the catalyst becomes not more than 0.1% by weight in the step (2).

The temperature of the slurry liquid phase portion and the temperature of the precipitate in the form of a cake given after water is drawn out and before the precipitate is dried are each preferably in the range of 10 to 40° C.

It is preferable that in the step (1), pH for forming the precipitate of the catalyst precursor is in the range of 5 to 9, and the concentration of the precipitate of the catalyst precursor in the slurry solution is in the range of 0.5 to 12% by weight in terms of a metal hydroxide.

It is preferable that in the step (4), the temperature and the pressure are controlled so that the water content of the catalyst precursor after drying may become 8 to 17% by weight, and thereafter, the catalyst precursor is calcined.

It is preferable that in the step (4), drying of the precipitate in the form of a cake is carried out at a temperature of 100 to 400° C.

It is preferable that the catalyst is molded by tablet making.

It is preferable that in the step (4), calcining of the catalyst precursor after drying is carried out at a temperature of 280 to 690° C.

The copper-based catalyst of the present invention is characterized by being obtained by reducing a catalyst obtained by the above preparation process at a temperature of higher than the catalytic reaction temperature but lower than the calcining temperature in a stream of a hydrogen-containing gas, and is preferably obtained by reducing the catalyst at a temperature of 300 to 550° C.

The pretreatment method of a copper-based catalyst of the present invention is characterized by comprising reducing a catalyst obtained by the above preparation process at a temperature of 300 to 550° C. in a stream of a hydrogen-containing gas before the catalytic reaction, and the hydrogen concentration of the hydrogen-containing gas is preferably in the range of 0.1 to 10% by volume.

Advantageous Effects of Invention

The preparation process and the pretreatment method of the present invention have high reproducibility, and the resulting catalyst exhibits high activity, maintains the high activity over a long period of time and is excellent in durability. The catalytic activity maintenance effect of the catalyst is remarkable, and excellent activity and durability which cannot be expected from copper-based multi-component catalysts for methanol synthesis used or proposed at present are obtained. The present invention is extremely useful particularly industrially. According to the process for preparing a copper-based catalyst of the present invention, further, a catalyst having the above characteristics can be prepared through more simplified preparation steps than those of conventional processes. Decrease of the number of steps is extremely useful because it leads to lowering of the production cost.

BRIEF DESCRIPTION OF DRAWING

FIG. 1 shows a chart of thermobalance analysis of a cake 1 and a cake 2 described in Example B1.

DESCRIPTION OF EMBODIMENTS

Details of a copper-based catalyst prepared by the preparation process of the invention are described below, and then details of the process for preparing a copper-based catalyst and the pretreatment method of a copper-based catalyst of the invention are described. The copper-based catalyst prepared by the preparation process of the invention is also referred to as a "copper-based catalyst" simply hereinafter.

Copper-Based Catalyst

The copper-based catalyst prepared by the preparation process of the invention is a catalyst composed of metal oxides containing copper oxide as an essential component, and preferably further contains at least one oxide selected from zinc oxide, aluminum oxide, zirconium oxide, gallium oxide and silicon oxide.

The copper-based catalyst prepared by the preparation process of the invention is particularly preferably a catalyst composed of metal oxides containing copper oxide, zinc oxide and aluminum oxide as essential components and containing zirconium oxide, gallium oxide and silicon oxide as arbitrary components.

The copper-based catalyst may further contain other oxides within limits not detrimental to the spirit of the present invention. As other components, oxides of noble metals such as palladium are usually used in some cases because of high reactivity, but the copper-based catalyst prepared by the preparation process of the invention tends to be able to exert high catalytic performance even if the noble metal oxide is not used.

The proportions of the components are as follows. Based on 100% by weight of the whole catalyst, the proportion of copper oxide is in the range of usually 20 to 60% by weight, preferably 30 to 50% by weight; the proportion of zinc oxide is in the range of usually 10 to 50% by weight, preferably 20 to 40% by weight; the proportion of aluminum oxide is in the range of usually 2 to 10% by weight, preferably 4 to 8% by weight; the proportion of zirconium oxide is in the range of usually 0 to 40% by weight, preferably 10 to 20% by weight; the proportion of gallium oxide is in the range of usually 0 to 10% by weight, preferably 0.1 to 5% by weight; and the proportion of silicon oxide is in the range of usually 0 to 2% by weight, preferably 0.0 to 0.9% by weight, more preferably 0.3 to 0.9% by weight. The present invention can be favorably applied to the preparation of a copper-based catalyst having such proportions of the components. By properly determining composition according to proper formulation of the catalyst and the desired reaction, catalytic performance suitable for the reaction can be obtained.

In the copper-based catalyst of the invention, silicon oxide may be derived from colloidal silica or water-dissolved silica. The colloidal silica and the water-dissolved silica may be used in combination. In the case where a copper-based catalyst is prepared by adding sodium silicate (water glass) or potassium silicate, a copper-based catalyst having the prescribed effect cannot be sometimes obtained though such a compound is also a silicon compound.

In the case where colloidal silica is used, it is preferable to use colloidal silica having a sodium oxide content of less than 0.1% by weight, particularly not more than 0.06% by weight, i.e., colloidal silica substantially having no sodium content. Many grades of colloidal silica have a sodium oxide content of about 0.2 to 0.6% by weight.

In the case where water-dissolved silica is used, natural fresh water, tap water, well water, industrial water or the like is employable. Such water contains dissolved silica in an amount of about 20 ppm to 100 ppm. The dissolved silica is silica whose test water is measured by absorptiometry using molybdenum yellow method or molybdenum blue method (said silica being commonly called "colorimetric silica").

Process for Preparing Copper-Based Catalyst

The process for preparing a copper-based catalyst of the invention is important in order to bring out performance of a catalyst of proper composition to the most. One embodiment of the process for preparing a copper-based catalyst of the invention is also intended to simplify the molding steps, and optimization of composition of the catalyst according to the desired reaction is important in order to bring out performance of the catalyst to the most, as described above.

The aforesaid catalyst (aforesaid conventional catalyst for methanol production) is generally prepared by mixing A liquid made of an acidic metal salt solution (e.g., A liquid made of an aqueous solution containing a water-soluble salt of a metal component) with B liquid made of a precipitant solution (e.g., B liquid made of an aqueous solution of a precipitant containing a basic substance) to form a precipitate that becomes a catalyst precursor, properly aging, then carrying out washing in order to remove the precipitant, drying the washed precipitate and then carrying out calcining treatment at 280 to 690° C. to form a calcined product.

The present invention is characterized in that in the above washing to remove the precipitant (more particularly alkali metal of the precipitant component), a slurry solution containing a precipitate of a catalyst precursor and a wash liquid are brought into contact with each other to wash the precipitate, with substantially keeping the suspended state. The expression "substantially keeping the suspended state" means a state where the slurry solution keeps fluidity. The condition of the precipitate, e.g., fluidity, varies depending upon the particle size and the composition of the precipitate, even if the content of the precipitate in the solution is the same. As a measure, therefore, a state where the weight concentration of the precipitate in the slurry solution is in the range of 0.5 to 12% by weight in terms of a metal hydroxide is defined as "substantially keeping the suspended state".

The acidic metal salt solution is preferably an aqueous solution containing a water-soluble salt of a metal component, and the precipitant solution is preferably an aqueous solution of a precipitant containing a basic substance. The wash liquid is preferably water. Water used as the wash liquid is water substantially containing no alkali metal, and is desirably water having an alkali metal content of not more than 100 ppm, particularly not more than 10 ppm, more particularly not more than 1 ppm. Such water substantially containing no alkali metal is also referred to as "clean water" in the present invention. As the metal component, copper is an essential component, and zinc, aluminum, zirconium, gallium and silicon can be mentioned. A preferred embodiment is described below, but the present invention is not limited to the embodiment.

For mixing the A liquid with the B liquid to form a precipitate, not only a method wherein the A liquid and the B liquid are mixed all together to precipitate the components of the A liquid but also a method wherein the A liquid is divided into two or more portions, then the A liquid made of an aqueous solution containing one or more components of the water-soluble salts of the metal components is mixed with the B liquid made of an aqueous solution of a precipitant containing a basic substance to precipitate the components of the A liquid, and to the liquid containing the precipitate is added the A liquid made of an aqueous solution containing the residual components to likewise precipitate the components is adopted. For the mixing, other various methods are available. The mixed liquid of the A liquid and the B liquid to form a precipitate of a catalyst precursor has pH of preferably 5 to 9.

As the water-soluble salts of metal components other than the silicon component among the above metal components, nitrate and nitrite both of which have excellent water solubility are preferably used. As the basic substances, alkali metal salts, such as sodium carbonate, potassium carbonate, sodium hydroxide and potassium hydroxide, are preferably used, and according to circumstances, ammonia, alkanolamine, amine, etc. can be also used. When sodium hydroxide or potassium hydroxide is used, blowing of $CO_2$ gas is also used in combination.

In the present invention, it is preferable to allow the precipitate to adsorb colloidal silica or water-dissolved silica in the formation, aging or washing of the precipitate. In order to allow the precipitate to adsorb colloidal silica in the formation of the precipitate, a method of adding colloidal silica to at least one of the A liquid and the B liquid, a method of mixing the A liquid with the B liquid in water containing colloidal silica, or the like is adopted. From the fact that the colloidal silica is not actually introduced into the supernatant liquid in the formation or aging of the precipitate and that the silica component does not actually flow out even if washing is carried out after the colloidal silica is adsorbed, it can be understood that the colloidal silica is not merely mixed with the precipitate but is adsorbed on the precipitate. In order to allow the precipitate to adsorb water-dissolved silica, a method of preparing an aqueous solution containing a water-soluble salt of a metal component or an aqueous solution containing a basic substance by the use of water containing dissolved silica, a method of washing the precipitate by the use of water containing dissolved silica, or the like is adopted.

After the formation of the precipitate, aging is properly carried out, and then washing is carried out in order to obtain a catalyst precursor of high activity. This washing is carried out in order to remove the alkali metal of the precipitant component, and it is known that if the washing is insufficiently carried out and if a large amount of the alkali metal remains, activity of the catalyst is markedly lowered in the methanol production that is carried out later. On that account, washing is usually carried out until the alkali metal is removed to such an extent that the alkali metal exerts no influence on the methanol synthesis reaction or the like.

As a usual washing method, the following method is used. The precipitate in the slurry is subjected to filter filtration by compression or the like to remove water together with the dissolved precipitant, and then clean water is added to the precipitate to redisperse the precipitate in the water added. The resulting slurry wherein the precipitate is dispersed in water is filtered again. A series of these operations are repeated until the concentration of the alkali metal of the precipitant component in the precipitate becomes the aimed concentration or lower. Or, after the slurry is filtered in a filter plate to prepare a precipitate in the form of a cake, and then wash water is made to flow over the filter plate (or the precipitate in the form of a cake) to expel the filtrate present in the precipitate in the form of a cake by substitution, that is, substitution washing is carried out. Most of the alkali metal of the precipitant component is usually present in water because a compound having high water solubility is used. Therefore, through the above operations, the alkali metal of the precipitant component is efficiently removed by wash water.

According to the studies by the present inventors, however, it has been confirmed that in the above method, the alkali metal frequently remains in the precipitate in a concentration much higher than the alkali metal concentration in the filtrate in spite that the alkali metal concentration in the filtrate is sufficiently lowered. That is to say, the alkali metal is not readily eluted into the filtrate. Accordingly, even if the alkali metal concentration in the filtrate is lowered, it does not necessarily follow that the alkali metal is removed from the precipitate.

According to further studies by the present inventors, it has been found that in the above method of washing with clean water after formation of the cake, it is necessary to allow the slurry solution to stand for at least 2 hours with stirring after addition of clean water, in order that the alkali metal concentration in the filtrate and the alkali metal concentration in the precipitate may become the same as each other. The cause of this is presumed to be that the alkali metal is ionically bonded to the precipitate, and the alkali metal is slowly dissolved in water at equilibrium, or the precipitate is formed into a cake by filtration, so that even if water is then added in order to disperse the precipitate, the precipitate is hardly diffused and the alkali metal remaining in the precipitate is hardly removed. Therefore, when filtration and dispersion are repeated, at least a number of repetition times are necessary. It is desirable to remove the alkali metal until the alkali metal content in the precipitate becomes not more than 0.1% by weight based on the precipitate. However, washing by repetition of such filtration and diffusion into water needs a long time.

In the prior techniques, there is no description of a washing method particularly, and with regard to the reproduction of the catalytic activity, satisfactory result is not necessarily obtained particularly in the scale-up case (e.g., JPA-1995-8799, JPA-1995-39755, and JPA-1998-272361).

As a result of further studies in the light of the above circumstances, the present inventors have found that in the washing to remove the alkali metal of the precipitant component, it is necessary to continuously bringing the slurry solution containing the precipitate of the catalyst precursor and the wash liquid into contact with each other to wash the precipitate, with substantially keeping the suspended state, in order to efficiently remove the alkali metal. In particular, the acidic metal salt solution containing copper and the precipitant solution are both aqueous solutions, so that in order to efficiently remove the alkali metal, it is preferable that these aqueous solutions are mixed in water to form a precipitate of a catalyst precursor, and thereafter dissolution equilibrium of the alkali metal is sufficiently reached in such a state that the precipitate is highly dispersed in water, and the slurry solution and clean water are brought into contact with each other with substantially keeping the suspended state.

The purpose of always bringing clean water and the slurry solution into contact with each other is to feed water containing no alkali metal to thereby substitute the water for water in which an alkali metal is dissolved, and the state where dissolution equilibrium of the alkali metal is sufficiently reached means a state where the error in a change of electrical conductance in the slurry solution becomes not more than 5% of the original electrical conductance in one hour after the precipitate is dispersed in water in a concentration of 2% by weight.

A lower content of the alkali metal is preferable, but treatment to bring the content as close to zero as possible needs extremely much time. In the present invention, therefore, removal of the alkali metal until the alkali metal content in the precipitate becomes not more than 0.1% by weight is adequate, or it is preferable to remove the alkali metal until the alkali metal concentration in the finally obtained catalyst becomes not more than 0.1% by weight.

That is to say, it is particularly preferable in the invention that without forming the resulting precipitate into a cake by filtration but with keeping the slurry state, clean water is added while the slurry liquid phase portion is continuously drawn out to thereby remove the alkali metal of the precipitant component together with the liquid phase portion drawn out. The slurry concentration (concentration of precipitate of catalyst precursor) is not specifically restricted, and as long as the precipitate can be maintained in a highly dispersed state, the slurry concentration is not restricted. Taking operating properties into account, the slurry concentration is practically not more than 12% by weight. If the slurry concentration is lower than 0.5% by weight, a large apparatus is necessary, and consequently, economical efficiency is sometimes lowered. The slurry concentration is a value in terms of a metal hydroxide. In the above method, treatment is carried out in such a state that the precipitate and water are always in contact with each other, so that the contact time is long, and the washing time can be markedly shortened as compared with the operations of filtration and redispersion in water. The temperature of the slurry liquid phase portion is preferably in the range of 10 to 40° C.

Generally, repetition of operations consisting of compressing the precipitate as strongly as possible to squeeze water out, then newly adding wash water and squeezing water out again can remove the alkali metal more efficiently. However, in the case of removal of the alkali metal from the catalyst precursor composed of metal oxides containing copper oxide as an essential component (e.g., metal oxides containing copper oxide, zinc oxide and aluminum oxide as essential components and containing zirconium oxide, gallium oxide and silicon oxide as arbitrary components), it is more effective to substitute wash water while keeping the slurry state, for the aforesaid reason. The slurry concentration is preferably maintained at the same concentration during the washing.

The apparatus to carry out operations of sufficiently reaching dissolution equilibrium of the alkali metal of the precipitant component in such a state that the precipitate is highly dispersed in water and always bringing the precipitate into contact with clean water has only to be an apparatus which is made up of a part for drawing out water from the slurry, a part for newly adding clean water and a part for mixing the newly added water with the slurry given after water is drawn out and in which these parts are connected so that the slurry can be circulated.

For example, a so-called cake-less filter (dynamic filter) equipped with traction mechanism which can inhibit thickening of a filter layer of a filter cake as much as possible during removal of water is adoptable. Specifically, rotary cylindrical cake-less filter, Shriver type filter thickener, multi-chamber cylindrical vacuum filter (Oliver type filter), centrifugation type slurry filter or the like is employable The slurry washed as above can be concentrated as such (for example, by drawing the slurry liquid phase portion outside the system without adding water) and subjected to spray drying, but generally, the slurry is subjected to pressure filtration to give a precipitate in the form of a cake. In this case, vacuum filter, filter press, centrifugal dehydration filter or the like is employable. The temperature of the precipitate in the form of a cake prior to drying is preferably in the range of 10 to 40° C.

The resulting precipitate in the form of a cake becomes metal oxides by subjecting it to drying and calcining. The apparatus for the drying and calcining is not specifically restricted, and a general dryer is used. When the resulting catalyst is used as an industrial catalyst, it is generally molded prior to use. As the method to mold the catalyst, extrusion or tablet making is generally used. When the catalyst is used by filling it into a fixed bed reactor, tablet making method in which the catalyst is hardly pulverized or broken, variability of pressure loss is small, and tablets of uniform shapes are obtained is preferable. In the case of the tablet making, a powder catalyst is filled in a mortar of a tablet making machine, and a rod is pushed down to perform molding. The powder is first subjected to heat treatment to remove extra water content. In this heat treatment, calcining may be also carried out. However, if calcining is carried out prior to molding, the catalyst with higher strength may not be obtained after molding. On the other hand, if calcining is carried out after molding, because of the dehydration shrinkage that takes place during the calcining, the catalyst with higher strength may be obtained. Therefore, before the tablet making, the powder is usually dried at a temperature lower than the temperature of actual calcining. That is to say, drying is carried out at a temperature of usually 100° C. to the calcining temperature, preferably a temperature lower than the calcining temperature by 100 to 300° C. The particle diameters of the powder must be made uniform so that the powder can be filled in the mortar rapidly and homogeneously. In order to make the catalyst particles uniform, screening of the catalyst is usually carried out after drying, but it is also possible that the precipitate in the form of a cake is formed into a slurry and the slurry is subjected to spray granulation. The size of the particle is generally in the range of about several tens µm and sub-mm though it depends upon the size of the mortar. In the tablet making, molding of the powder is carried out more easily as the rod of the tablet making machine moves more smoothly, so that a lubricant that enables the rod to smoothly move, such as graphite, is generally added to the catalyst powder. Although the amount of the lubricant can be properly controlled according to the molded state of the molded product, the lubricant is generally added in an amount of 1 to 10% by weight based on the catalyst powder.

In the tablet making, the powder is solidified by a compressive force and thereby molded, and it is preferable that the strength of the resulting molded product becomes as high as possible by application of a small compressive force. In order to increase bonding power of the powder particles, a certain amount of water is generally introduced into the powder. Unless the water is homogenously dispersed in the powder, variability of strength is brought about. According to circumstances, therefore, standing is carried out in order to homogeneously disperse water. With regard to the amount of water added, an optimum amount of water is examined in advance from the relationship between the strength and the amount of water.

Accordingly, molding of the powder, particularly tablet making, has been considered to need, as pretreatments, many steps, such as pulverization with making the particle diameters of the catalyst precursor uniform, addition of a lubricant and homogeneous mixing, and addition of water and homogeneous mixing.

In the light of such complicated operations, the present inventors have studied, and as a result, they have found that it is particularly preferable to adjust water content of the catalyst precursor after drying to 8 to 17% by weight in spite of necessity for tablet making (the water content in the invention is a value based on the water content in the catalyst having been calcined at 600° C. being zero). That is to say, the present inventors have also found that if the amount of water remaining in the catalyst is adjusted by controlling the heat treatment temperature of the catalyst precursor and the pressure, the aforesaid addition of water, mixing for homogeneous dispersion and standing can be omitted, and even if the steps are simplified, a catalyst having high activity and high durability can be prepared. In this case, when the same treatment temperature is used, a large difference in content of residual water is not observed even if the drying time is somewhat different. The lower limit of the treatment temperature is not lower than 100° C., preferably not lower than 200° C., more preferably not lower than 250° C., though it depends upon the tablet making conditions. The upper limit of the treatment temperature is 550° C., preferably 400° C., more preferably 300° C. Although the drying time is not specifically restricted, it is preferably not less than 0.1 hour, more preferably not less than 0.5 hour. There is no need to determine the upper limit of the drying time, but taking productivity into account, the upper limit is 10 hours, preferably 5 hours. The pressure in the drying step is preferably in the range of vacuum to 0.2 MPa, more preferably vacuum to normal pressure. The drying step may be carried out not only in air but also in a stream of an inert gas such as nitrogen.

In the case of the catalyst of the invention, the water content dependent upon the heat treatment temperature is preferably in the range of 8 to 17% by weight, and by controlling the drying step in such a manner, a catalyst of high activity and high durability can be obtained even if steps of addition of water, mixing and standing are not carried out. Moreover, a catalyst having high crushing strength, which does not suffer occurrence of cracks when it is subjected to molding, particularly tablet making, can be obtained.

The water content and the heat treatment temperature frequently have a given relationship to each other. This relationship can be determined by, for example, thermobalance measurement. The relationship is not specifically restricted by the shape of the apparatus or the like, and even if drying is carried out by a general calcining machine, similar results are often obtained. After the pretreatment, the catalyst precursor is molded by, for example, tablet making. As the apparatus for this tablet making, a usual tablet making machine is used, and there is no specific limitation.

After the drying, the catalyst precursor is subjected to calcining treatment at a temperature of usually 280 to 690° C., preferably 350 to 680° C., particularly preferably 480 to 670° C., to give a calcined product. On the other hand, the precipitate on which colloidal silica has been adsorbed is subjected to calcining treatment at a temperature of usually 480 to 690° C., preferably 520 to 680° C., particularly preferably 560 to 670° C., to give a calcined product. The calcining is carried out in an oxygen atmosphere (usually in air), whereby the aforesaid metal components become oxides.

Reduction Treatment (Pretreatment)

The pretreatment method of the invention is characterized by reducing a copper-based catalyst at a temperature of higher than the catalytic reaction temperature but lower than the calcining temperature (e.g., temperature of 300 to 550° C.) in a stream of a reducing gas prior to the catalytic reaction. As the copper-based catalyst for use in the pretreatment, any catalyst properly selected from hitherto publicly known catalysts is employable as long as it is a catalyst composed of the aforesaid metal oxides (e.g., catalyst composed of metal oxides containing copper oxide, zinc oxide and aluminum oxide as essential components and containing zirconium oxide, gallium oxide and silicon oxide as arbitrary components). As the copper-based catalyst for use in the pretreatment, a copper-based catalyst obtained by the aforesaid preparation process of the invention is particularly preferable.

The copper-based catalyst obtained by the preparation process of the invention as above is preferably reduced under the specific conditions. The copper-based catalyst of the invention has catalytic action also in this stage, but it is preferable to reduce (pretreat) the copper-based catalyst of the invention by a reducing gas, e.g., a hydrogen-containing gas such as $H_2$ gas or $H_2$—$N_2$ mixed gas, prior to use of the copper-based catalyst for methanol synthesis or the like.

The reducing gas is preferably a hydrogen-containing gas. The hydrogen concentration of the hydrogen-containing gas is preferably in the range of 0.1 to 10% by volume. In the case of a hydrogen-containing gas having a hydrogen concentration of lower than 0.1% by volume, reduction takes time, and an economical problem frequently occurs. If the hydrogen concentration exceeds 10% by volume, abrupt reduction takes place, and there is a fear of doing damage to the copper-based catalyst.

When the copper-based catalyst is reduced by a reducing gas, it is preferable in the invention to carry out the reduction in a stream of a reducing gas under the conditions of a temperature of higher than the reaction temperature used in the production of methanol or the like but lower than the calcining temperature of the above calcining step. The lower limit of the reduction temperature is usually 300° C., preferably a temperature of more than 300° C., more preferably a temperature of 350° C. On the other hand, the upper limit is usually 550° C., more preferably 500° C. It is said that when a copper-based catalyst is treated at a high temperature of not lower than 300° C., the surface area of the reduced copper is generally decreased by sintering or the like to thereby lower activity. In the present invention, however, it has been found that reduction at a temperature of not lower than 300° C., preferably a temperature of more than 300° C., rather increases the surface area of copper, and this is surprising. However, if the temperature exceeds 550° C., sintering takes place, and there is possibility of decrease of surface area.

That is to say, this indicates that the copper-based catalyst of the invention is in such a form that (1) copper is hardly reduced at a low temperature and (2) copper is hardly sintered even at a high temperature, as compared with usually known copper-based catalysts. It is thought that such properties are connected to maintenance of catalytic activity over a long period of time and excellent durability. Moreover, by carrying out pretreatment wherein the catalyst is reduced in advance at a high temperature of preferably not lower than 300° C., more preferably more than 300° C., shortening of induction period in the initial stage of reaction and enhancement of catalytic activity can be realized.

In the copper-based catalyst of the invention, the aforesaid surprising tendency frequently appears especially when copper oxide which is an essential component (preferably, copper oxide, zinc oxide and aluminum oxide which are essential components and zirconium oxide, gallium oxide and palladium oxide which are arbitrary components) forms skeletons and among the skeletons colloidal silica or water-dissolved silica having been adsorbed when necessary is present as silicon oxide in a specific amount of usually of 0 to 2% by weight, preferably 0.0 to 0.9% by weight, more preferably 0.3 to 0.9% by weight. When the calcining treatment is carried out in a specific high temperature range of 480 to 690° C., such tendency becomes more marked.

Although the reason why the effect of the invention tends to be exhibited when a silicon compound is contained is unknown, the following hypothesis can be thought. It is thought that since the silicon component exerts a function of inhibiting transfer of a metal component in the catalyst, the catalyst exhibits high activity, maintains the high activity over a long period of time and has high durability, and this effect is exhibited also in the reduction treatment, that is, since the transfer of the metal component is likewise inhibited, sintering can be inhibited. It is considered that the effect becomes greater as the temperature in the pretreatment of the catalyst is raised, and as a result, the catalyst exhibits higher activity by virtue of the pretreatment conditions of the invention.

The catalyst obtained as above is used as it is or after granulated by an appropriate method or tablet making, and is used for, for example, the following reactions. The particle diameter and the shape of the catalyst can be arbitrarily selected according to the reaction system and the shape of the reactor.

Reaction

The copper-based catalyst of the invention and the reduced (pretreated) copper-based catalyst are useful for catalytic reactions, such as methanol synthesis reaction or its reverse reaction, methanol reforming reaction, and shift reaction or its reverse reaction, and they are particularly useful as catalysts for the reaction to synthesize methanol from hydrogen and carbon oxide or its reverse reaction.

When the catalyst is used for the reaction, the catalyst can be used as it is, as described above, but it is preferable to reduce the catalyst by a reducing gas such as $H_2$ gas or $H_2$—$N_2$ mixed gas prior to use.

In the case of methanol synthesis, hydrogen and a raw material gas composed of carbon oxide are allowed to react with each other on the catalyst to synthesize methanol. This reaction is carried out typically at a reaction temperature of 150 to 300° C. and a reaction pressure of 1 to 10 MPa. In the case of its reverse reaction, methanol can be decomposed into hydrogen and carbon oxide. This reaction is carried out typically at a reaction temperature of 200 to 400° C. and a reaction pressure of atmospheric pressure to 1 MPa. These reactions can be carried out in any of a gas phase and a liquid phase. As the solvents used when the reaction is carried out in a liquid phase, hydrocarbon-based solvents and water-insoluble to water-slightly soluble solvents are employable.

Action

With regard to the copper-based catalyst of the invention, copper oxide which is an essential component (preferably, copper oxide, zinc oxide and aluminum oxide which are essential components and zirconium oxide, gallium oxide, palladium oxide and silicon oxide which are arbitrary components) forms skeletons, and an alkali metal which inhibits activity is sufficiently removed. Therefore, by subjecting the catalyst to calcining treatment in the temperature range of, for example, 480 to 690° C. after drying step that is carried out when necessary, the catalyst exhibits high activity, maintains the high activity over a long period of time and has excellent durability.

According to the studies by the present inventors, it has been found that presence of an alkali metal in a catalyst accelerates crystallization of a metal oxide component in the catalyst to thereby decrease a specific surface area of the active component. For example, it has been made clear by the X-ray diffraction measurement of a catalyst that even if only 0.4% by weight of an alkali metal is present in a catalyst containing copper oxide, zinc oxide, aluminum oxide and zirconium oxide as main components, crystals of Cu (reduced state), zinc oxide, aluminum oxide and zirconium oxide considerably grow. On the other hand, it has been made clear that when a catalyst which contains copper oxide, zinc oxide, aluminum oxide and zirconium oxide as main components and from which an alkali metal is removed to an alkali metal content of 0.1% by weight is subjected to the same calcining and then subjected to X-ray diffraction measurement, crystals of Cu (reduced state), zinc oxide, aluminum oxide and zirconium oxide hardly grow. That is to say, by virtue of sufficient removal of an alkali metal, crystal growth of each component of the catalyst is inhibited, and high dispersibility can be maintained over a long period of time.

The copper-based catalyst prepared by the invention is a catalyst whose performance can be stably reproduced and which can be applied also to an industrial preparation process. Further, one embodiment of the process for preparing a copper-based catalyst of the invention can prepare the above copper-based catalyst through steps of smaller number than those of conventional processes, so that the invention is particularly useful as an industrial preparation process.

The present invention is further described with reference to the following examples, but it should be construed that the invention is in no way limited to those examples.

EXAMPLES

The following processes are all carried out at normal pressure.

Example A1

In distilled water, 5.6 kg of copper nitrate trihydrate, 4.1 kg of zinc nitrate hexahydrate, 1.4 kg of aluminum nitrate nonahydrate, 2.0 kg of zirconium nitrite dihydrate and 0.1 kg of colloidal silica ("Snowtex ST-O" available from Nissan Chemical Industries, Ltd., silicic anhydride ($SiO_2$) content: 20 to 21% by weight) were dissolved, to prepare 38 liters of an aqueous solution as A liquid. Separately from this, 15.7 kg of sodium carbonate decahydrate was dissolved in distilled water to prepare 38 liters of an aqueous solution as B liquid.

To 125 liters of distilled water vigorously stirred, the A liquid and the B liquid were dropwise added at the same time with adjusting pH to 7.0 to 7.4 (this method being referred to as "coprecipitation method"). The resulting mixture was allowed to stand for a whole day and night at 30° C. Thereafter, by the use of a rotary cylindrical cake-less filter having a filtration area of 1 $m^2$, 2.4 $m^3$ of distilled water at 25° C. was continuously fed and the slurry liquid phase portion was drawn out at the same rate, to obtain a precipitate. The precipitate was washed, and then the slurry liquid phase portion was drawn outside the system by a pressure filter without adding water, followed by recovering a cake. The weight concentration of the precipitate in the slurry was 1.5% by weight in terms of a metal hydroxide, the whole treatment time of the precipitate was 9 hours, and the filtrate electrical conductance was 60 mS/m. A part of the cake was withdrawn and redispersed in water so as to give a slurry of 2% by weight, and the filtrate electrical conductance was measured.

At the start, the filtrate electrical conductance was 30 mS/m, and after the slurry was allowed to stand for 1 hour, the filtrate electrical conductance became 31 mS/m.

The cake was dried at 110° C. and then calcined in air at 600° C. for 2 hours. The resulting catalyst had a sodium content of 0.03% by weight, and the specific surface area of the catalyst after calcining was 85 m$^2$/g.

Comparative Example A1

A precipitate obtained in the same manner as in Example A1 was filtered by a filter press having a filtration area of 1.2 m$^2$, and in this state, 2.5 m$^3$ of distilled water at 25° C. was passed through the filtration chamber to wash the precipitate, followed by recovering a cake. The whole treatment time of the precipitate was 7 hours, and the filtrate electrical conductance was 14 mS/m. A part of the cake was withdrawn and redispersed in water so as to give a slurry of 2% by weight, and the filtrate electrical conductance was measured. At the start, the filtrate electrical conductance was 20 mS/m, but after 1 hour, the filtrate electrical conductance became 280 mS/m, and equilibrium was not reached.

The cake was dried at 110° C. and then calcined in air at 600° C. for 2 hours. The resulting catalyst had a sodium content of 1.4% by weight, and the specific surface area of the catalyst after calcining was 32 m$^2$/g.

Comparative Example A2

A precipitate obtained in the same manner as in Example A1 was filtered by a filter press having a filtration area of 1.2 m$^2$, and the resulting cake was redispersed in 200 liters of distilled water at 25° C. over a period of 30 minutes (weight concentration of precipitate in slurry: 2.5% by weight in terms of metal hydroxide) and filtered immediately by a filter press again. These operations were repeated 3 times. The whole treatment time of the precipitate was 10 hours, and the filtrate electrical conductance was 30 mS/m. A part of the cake was withdrawn and redispersed in water so as to give a slurry of 2% by weight, and the filtrate electrical conductance was measured. At the start, the filtrate electrical conductance was 25 mS/m, but after 1 hour, the filtrate electrical conductance became 240 mS/m, and equilibrium was not reached.

The cake was dried at 110° C. and then calcined in air at 600° C. for 2 hours. The resulting catalyst had a sodium content of 1.3% by weight, and the specific surface area of the catalyst after calcining was 40 m$^2$/g.

Comparative Example A3

A precipitate obtained in the same manner as in Example A1 was filtered by a filter press having a filtration area of 1.2 m$^2$, and the resulting cake was redispersed in 200 liters of distilled water at 25° C. over a period of 30 minutes (weight concentration of precipitate in slurry: 2.5% by weight in terms of metal hydroxide) and continuously stirred for 2 hours, followed by filtration by a filter press again. These operations were repeated 3 times. The whole treatment time of the precipitate was 15 hours, and the filtrate electrical conductance was 11 mS/m. A part of the cake was withdrawn and redispersed in water so as to give a slurry of 2% by weight, and the filtrate electrical conductance was measured. At the start, the filtrate electrical conductance was 9 mS/m, but after 1 hour, the filtrate electrical conductance became 95 mS/m, and equilibrium was not reached.

The cake was dried at 110° C. and then calcined in air at 600° C. for 2 hours. The resulting catalyst had a sodium content of 0.54% by weight, and the specific surface area of the catalyst after calcining was 51 m$^2$/g.

Activity Evaluation

A reaction tube was filled with 2 ml of the catalyst obtained above, and a reducing gas consisting of 10% by volume of $H_2$ and 90% by volume of $N_2$ and having a temperature of 300° C. was passed through the reaction tube at 300° C. for 2 hours to reduce the catalyst. Thereafter, a mixed gas of 25% by volume of $CO_2$ and 75% by volume of $H_2$ was passed through the catalyst layer at a rate of 20 l/hr, and the reaction was performed under the conditions of a pressure of 5 MPa and a temperature of 250° C. The reaction generation gas was analyzed by a gas chromatograph to determine a relationship between the reaction time and the amount of methanol produced. The amount of methanol (g-MeOH/L-Cat/hr) produced in 5 hours after the initiation of the reaction is set forth in Table 1.

TABLE 1

|  | Treatment time (hr) | Na (wt %) | Amount of methanol produced (g-MeOH/L-cat/hr) |
| --- | --- | --- | --- |
| Ex. A1 | 9 | 0.03 | 550 |
| Comp. Ex. A1 | 7 | 1.4 | 320 |
| Comp. Ex. A2 | 10 | 1.3 | 350 |
| Comp. Ex. A3 | 15 | 0.54 | 500 |

Example B1

Cake 1: To 125 liters of distilled water vigorously stirred, the A liquid and the B liquid prepared in Example A1 were dropwise added at the same time at each rate of 200 ml/min (this method being referred to as "coprecipitation method"). The resulting mixture was allowed to stand for a whole day and night, and thereafter, the resulting precipitate was washed with 2.4 m$^3$ of distilled water in the same manner as in Example A1, followed by recovering a cake by a pressure filter.

Cake 2: A precipitate obtained in the same manner as that for the cake 1 was washed with 10 m$^3$ of distilled water in the same manner as in Example A1, followed by recovering a cake by a pressure filter.

The cake 1 recovered was dried at 500° C. for 2 hours. The water content of this cake was measured based on the catalyst having been treated at 600° C., and as a result, the water content was 1% by weight. Then, to the cake was added water with increasing the amount of water added by 2% by weight at a time until the amount of water added became 16% by weight from 2% by weight. It was confirmed that the amount of water added which made the strength highest was 13% by weight. Separately, the cake 1 and the cake 2 recovered were analyzed by a thermobalance (the results of the thermobalance measurement are shown in FIG. 1). It was confirmed from the thermobalance analysis that with regard to both of the cake 1 and the cake 2, the water content of 13% by weight corresponded to a water content given by heat treatment at 280° C.

After the resulting cake 1 was dried at 280° C. for 2 hours (water content: 13%), the particle diameters were made uniform to give a particle size of 50 to 100-mesh, then a lubricant was added, and the mixture was molded into tablets of 3 mm. After the molding, the tablets were calcined at 600° C. to obtain a catalyst as a product.

Reference Example B1

After the cake 1 obtained in Example B1 was dried at 500° C. for 2 hours (water content: 1%), the particle diameters were made uniform to give a particle size of 50 to 100-mesh, and a lubricant was added. Further, water was added in an amount of 12% by weight based on the catalyst, followed by standing for one day. The resulting powder was molded into tablets of 3 mm. After the molding, the tablets were calcined at 600° C. to obtain a catalyst as a product.

The crushing strength of the catalysts of Example 1 and Reference Example B1 on their side surfaces and the results of methanol synthesis reaction are set forth in Table 2. The methanol synthesis reaction was carried out in the same manner as above (activity evaluation).

It has been confirmed from Example B1 and Reference Example B1 that according to the preparation process of the invention, a catalyst of equal performance can be obtained even if addition of water and one day standing are not carried out.

TABLE 2

|  | Crushing strength | Amount of methanol produced (g-MeOH/L-cat/hr) |
|---|---|---|
| Ex. B1 | 40N | 570 |
| Ref. Ex. B1 | 39N | 570 |

Example C1

Preparation of Catalyst

In distilled water, 54.3 g of copper nitrate trihydrate, 39.1 g of zinc nitrate hexahydrate, 6.6 g of aluminum nitrate nonahydrate, 15.4 g of zirconium nitrite dihydrate and 1.26 g of colloidal silica ("Snowtex ST-O" available from Nissan Chemical Industries, Ltd.) were dissolved, to prepare 500 ml of an aqueous solution as A liquid. The "Snowtex ST-O" used herein is a transparent semi-opaque colloidal liquid having a silicic anhydride ($SiO_2$) content of 20 to 21% by weight, a sodium oxide ($Na_2O$) content of not more than 0.04% by weight, pH of 2 to 4, a particle diameter of 10 to 20 µm, a viscosity of not more than 3 cps/25° C., a specific gravity of 1.12 to 1.14/25° C. and a freezing point of 0° C.

Separately from the above, 139.0 g of sodium carbonate decahydrate was dissolved in distilled water to prepare 500 ml of an aqueous solution as B liquid.

To 400 ml of distilled water, the A liquid and the B liquid were dropwise added at the same time (this method being referred to as "coprecipitation method"). The resulting mixture was allowed to stand for a whole day and night. Thereafter, the resulting precipitate was washed with distilled water in the same manner as in Example A1, then dried at 110° C. for 2 hours at normal pressure and calcined in air at 600° C. for 2 hours, whereby a solid (I) corresponding to the desired copper-based catalyst (I) was obtained.

The resulting solid (I) had composition of CuO of 45.2% by weight, ZnO of 27.1% by weight, $Al_2O_3$ of 4.5% by weight, $ZrO_2$ of 22.6% by weight and $SiO_2$ of 0.6% by weight.

Influence of Reduction Temperature

A reaction tube was filled with 0.2 g of the solid (I) obtained above, and a reducing gas consisting of 5% by volume of $H_2$ and 95% by volume of Ar was passed through the reaction tube at each of the temperatures shown in Table 3 for 2 hours to reduce the solid. Thereafter, a gas consisting of 2.5% by volume of $N_2O$ and 97.5% by volume of He was passed through the reaction tube at 40° C., and a surface area of copper was calculated from the amount of $N_2O$ adsorbed.

The results are set forth in Table 3. In this catalyst, $S_{300}$ was calculated at 15.4 $m^2$/g-cat, and $S_{500}/S_{300}$ was calculated at 1.4.

TABLE 3

| Reduction temperature (° C.) | Cu surface area ($m^2$/g-cat) |
|---|---|
| 200 | 12.4 |
| 250 | 13.7 |
| 300 | 15.4 |
| 350 | 17.4 |
| 400 | 19.9 |
| 450 | 21.5 |
| 500 | 21.6 |
| 550 | 21.7 |

Activity Test of Catalyst in Methanol Synthesis

A reaction tube was filled with 2 ml of the catalyst obtained above, and a reducing gas consisting of 5% by volume of $H_2$ and 95% by volume of $N_2$ was passed through the reaction tube at a reduction temperature of 400° C. for 2 hours to reduce the catalyst. According to the results in Table 3, the catalyst having been subjected to reduction treatment had a Cu surface area of 19.9 $m^2$/g-cat. After the reduction treatment, a mixed gas of 25% by volume of $CO_2$ and 75% by volume of $H_2$ was passed through the catalyst layer at a rate of 20 l/hr, and the reaction was performed under the conditions of a pressure of 5 MPa and a temperature of 250° C. The reaction generation gas was analyzed by a gas chromatograph to determine a relationship between the reaction time and the amount of methanol produced.

The amount of methanol produced was 600 g-MeOH/L-Cat/hr.

Reference Example C1

The same activity test as in Example C1 was carried out, except that a catalyst obtained by treating the catalyst of Example C1 at a reduction temperature of 250° C. was used.

The amount of methanol produced was 430 g-MeOH/L-Cat/hr in the initial stage, and the activity slowly rose, but stable performance was not reached even after 2 months.

Reference Example C2

The same activity test as in Example C1 was carried out, except that a catalyst obtained by treating the catalyst of Example C1 at a reduction temperature of 600° C. was used.

The amount of methanol produced was 510 g-MeOH/L-Cat/hr.

The invention claimed is:

1. A process for preparing a copper-based catalyst, which is a process for preparing a catalyst composed of metal oxides containing copper oxide as an essential component and comprises the following steps:
   (1) a step of bringing an acidic metal salt solution containing copper and a precipitant solution into contact with each other to obtain a slurry solution containing a precipitate of a catalyst precursor,
   (2) a step of continuously bringing the slurry solution and a wash liquid into contact with each other to wash the precipitate, while keeping a suspended state where the weight concentration of the precipitate in the slurry solution is in the range of 0.5 to 12% by weight in terms of a metal hydroxide,
   a step of obtaining the precipitate washed in the step (2) from the slurry solution, and
   a step of drying and calcining the precipitate.

2. The process for preparing a copper-based catalyst as claimed in claim 1, wherein the catalyst composed of metal oxides containing copper oxide as an essential component further contains at least one oxide selected from zinc oxide, aluminum oxide, zirconium oxide, gallium oxide and silicon oxide.

3. The process for preparing a copper-based catalyst as claimed in claim 1, wherein the catalyst composed of metal oxides containing copper oxide as an essential component is a catalyst composed of metal oxides containing copper oxide, zinc oxide and aluminum oxide as essential components and containing zirconium oxide, gallium oxide and silicon oxide as arbitrary components.

4. The process for preparing a copper-based catalyst as claimed in claim 1, wherein the wash liquid is water.

5. The process for preparing a copper-based catalyst as claimed in claim 1, wherein the acidic metal salt solution containing copper and the precipitant solution are both aqueous solutions, and
   after these aqueous solutions are mixed in water to form a precipitate of a catalyst precursor in the step (1), dissolution equilibrium of an alkali metal of the precipitant component is reached in such a state that the precipitate is dispersed in water, and the slurry solution and a wash liquid comprising water are brought into contact with each other to wash the precipitate, with keeping the suspended state, in the step (2),
   wherein the state where dissolution equilibrium of the alkali metal is reached means a state where the error in a change of electrical conductance in a slurry solution obtained by dispersing the precipitate in water in a concentration of 2% by weight becomes not more than 5% of the original electrical conductance in one hour after the dispersion.

6. The process for preparing a copper-based catalyst as claimed in claim 5, wherein the step (2) includes a step of continuously carrying out drawing of the slurry liquid phase portion and feeding of the wash liquid comprising water to remove the alkali metal of the precipitant component, and the step (2) is followed by:

(3) the step of obtaining a precipitate from the slurry solution by drawing the slurry liquid phase portion from the slurry solution outside the system without adding water to thereby increase the concentration of the catalyst precursor contained in the slurry solution and to obtain a precipitate in the form of a cake, and (4) the step of drying and calcining the precipitate in the form of a cake to obtain metal oxides.

7. The process for preparing a copper-based catalyst as claimed in claim 6, wherein the precipitant is an alkali metal salt, and
   the alkali metal is removed until the concentration of the alkali metal contained in the catalyst becomes not more than 0.1% by weight in the step (2).

8. The process for preparing a copper-based catalyst as claimed in claim 6, wherein the temperature of the slurry liquid phase portion and the temperature of the precipitate in the form of a cake given after water is drawn out and before the precipitate is dried are each in the range of 10 to 40° C.

9. The process for preparing a copper-based catalyst as claimed in claim 5, wherein in the step (1), pH for forming the precipitate of the catalyst precursor is in the range of 5 to 9.

10. The process for preparing a copper-based catalyst as claimed in claim 6, wherein in the step (4), the temperature and the pressure are controlled so that the water content of the catalyst precursor after drying becomes 8 to 17% by weight, and thereafter, the catalyst precursor is calcined.

11. The process for preparing a copper-based catalyst as claimed in claim 10, wherein in the step (4), drying of the precipitate in the form of a cake is carried out at a temperature of 100 to 400° C.

12. The process for preparing a copper-based catalyst as claimed in claim 10, wherein the catalyst is molded by tablet making.

13. The process for preparing a copper-based catalyst as claimed in claim 10, wherein in the step (4), calcining of the catalyst precursor after drying is carried out at a temperature of 280 to 690° C.

* * * * *